United States Patent [19]
Trenkle et al.

[11] Patent Number: 5,269,169
[45] Date of Patent: * Dec. 14, 1993

[54] METHOD AND APPARATUS FOR SIMULTANEOUSLY ANALYZING AROMA EMITTED FROM THE INTERIOR AND EXTERIOR OF LIVING FRUIT

[75] Inventors: Robert W. Trenkle, Brielle; Braja D. Mookherjee, Holmdel; Michael J. Zampino, Roselle Park; Richard A. Wilson, Westfield; Subha M. Patel, Bridgewater, all of N.J.

[73] Assignee: International Flavors & Fragrances Inc., New York, N.Y.

[*] Notice: The portion of the term of this patent subsequent to Nov. 23, 2010 has been disclaimed.

[21] Appl. No.: 988,377

[22] Filed: Dec. 9, 1992

[51] Int. Cl.⁵ ............................................. G01N 31/00
[52] U.S. Cl. ..................................... 73/23.34; 73/23.2
[58] Field of Search ................ 73/23.34, 23.2; 422/83, 422/98

[56] References Cited

U.S. PATENT DOCUMENTS

| | | | |
|---|---|---|---|
| 3,902,851 | 9/1975 | Dravnieks | 73/23.34 |
| 4,770,027 | 9/1988 | Ehara et al. | 73/23.34 |
| 4,884,435 | 12/1989 | Ehara | 73/23.34 |
| 5,136,805 | 8/1992 | Mookherjee | 47/69 |
| 5,149,504 | 9/1992 | Tanaka | 73/23.34 |
| 5,177,994 | 1/1993 | Moriizumi et al. | 73/23.34 |

Primary Examiner—Herzon E. Williams
Assistant Examiner—Valerie Francies
Attorney, Agent, or Firm—Arthur L. Liberman

[57] ABSTRACT

A process for quantitatively and qualitatively substantially continuously analyzing the aroma emitted and rates of emission of the components thereof:
  (I) from within; and
  (II) from the outer surface of a living fruit using simultaneously-operating aroma trapping devices connected to (a) the outer surface of the living fruit and (b) an internal portion of the living fruit. Also described is apparatus for carrying out such a process. The living fruit may, for example, be a living pineapple or a living nectarine growing on a nectarine tree.

7 Claims, 7 Drawing Sheets

FIG. 3-C GC MASS SPECTRUM

METHOD AND APPARATUS FOR SIMULTANEOUSLY ANALYZING AROMA EMITTED FROM THE INTERIOR AND EXTERIOR OF LIVING FRUIT

BACKGROUND OF THE INVENTION

Our invention concerns a process for quantitatively and qualitatively substantially continuously analyzing the aroma emitted and rates of emission of the components thereof from within and from the outer surface of a living fruit simultaneously and apparatus for carrying out such a process.

Uses of aromas evolved from living fruits are highly sought after in the perfumery and flavor arts. Great difficulty has been experienced in attempting to capture and reproduce actual aroma ingredients of the living fruit.

U.S. Pat. No. 5,136,805 issued on Aug. 11, 1992 describes an air-tight flexible transparent container containing at least one living flower immersed in an aqueous suspension. Described in U.S. Pat. No. 5,136,805 is an article useful (i) for display purposes; and/or (ii) for analysis of the head space in the container above the living flower when the container is fitted with a tube effecting communication of the internal 3-space (internal volume) of the container with outside analytical means and/or (iii) for aromatizing the environment surrounding the container when the container is fitted with a wick effecting communication of the internal 3-space (internal volume) of the container with the environment surrounding the container. However, U.S. Pat. No. 5,136,805 does not teach or infer a technique for quantitatively and qualitatively substantially continuously analyzing the aroma emitted and rates of emission of the components thereof from within and from the outer surface of a living fruit simultaneously.

SUMMARY OF THE INVENTION

Our invention is drawn to a process for quantitatively and qualitatively substantially continuously analyzing the aroma emitted and rates of emission of the components thereof:
(i) from within; and
(ii) from the outer surface of a living fruit, simultaneously.

Examples of such living fruits are living pineapples and living nectarines. Examples of living nectarines are nectarines growing on a tree such as the red jewel nectarine tree (disclosed and claimed in U.S. Plant Pat. No. 8,013 issued on Oct. 27, 1992) and the red diamond nectarine tree (disclosed and claimed in U.S. Plant Pat. No. 3,165).

Our process comprises the steps of:
(a) removing a cylindrical core section from a section of the living fruit to form a core void;
(b) placing a first trapping tube (connected to a vacuum pump) into the core void;
(c) applying an enclosure containing a second trapping tube (connected to a vacuum pump) to a portion of unbroken surface of the same living fruit in a sealably affixable manner;
(d) engaging both vacuum pumps; and
(e) analyzing the substances trapped and the trapping tubes on a substantially continuous basis.

Apparatus for carrying out such a process is also intended to be part of our invention.

DETAILED DESCRIPTION OF THE INVENTION

Our invention covers a process for quantitatively and qualitatively substantially continuously analyzing the aroma emitted and rates of emission of the components thereof:
(i) from within; and
(ii) from the outer surface of
a living fruit simultaneously consisting essentially of the steps of:
(a) providing a living fruit located on a given central axis having an outer surface, a substantial portion of which is located at a given distance from the central axis and an inner volume surrounding said central axis and encompassed by said outer surface;
(b) removing a depth core section from said inner volume running from said outer surface to a depth of from about halfway up to entirely to the central axis, into said inner volume along a directional vector extending substantially radially from said central axis to said outer surface within said inner volume;
(c)-1: providing first analytical apparatus means comprising a first trapping tube means attached to first negative pressure pump means associated with first chemical analysis means (e.g., GC-mass spectral and infrared analytical equipment);
(c)-2: providing second analytical apparatus means comprising a second trapping tube means attached to second negative pressure pump means associated with second chemical analysis means;
(d) providing a hollow flexible enclosure means (e.g., a spherical cup-like enclosure) having an inner enclosure means void and an outer enclosure means surface encompassing said void and terminating at an enclosure rim means, said void being defined by said outer enclosure means surface and said enclosure rim means, an insertion orifice extending from said outer enclosure means surface to said inner enclosure means void, said enclosure means being capable of sealably gripping an unbroken portion of said outer surface of said living fruit at said enclosure rim means;
(e) causing said enclosure means to sealably grip said portion of said outer surface of said living fruit at said enclosure rim means;
inserting said first trapping tube means into said core section void along said directional vector;
(g) inserting said second trapping tube means through said insertion orifice causing it to be extended into said enclosure means void;
(h) simultaneously engaging said first negative pressure pump means and said second pressure pump means whereby components of the aroma evolving from said outer surface of said living fruit are entrapped in said second trapping tube means and components of the aroma evolving from within said living fruit are entrapped in said first trapping tube means, simultaneously; and
(j) analyzing the contents of said first trapping tube means using said first chemical analysis means and said second trapping tube means using said second chemical analysis means substantially continuously and substantially simultaneously.

Of course, when the living fruit is one that has a pit such as a peach or a nectarine or a plum, then obviously the depth core can only extend to the outer surface of the pit, and preferably the depth core should extend about two-thirds of the way into the fruit without touching the surface of the pit. Thus, for example, in the case of a pineapple the depth core would be about $\frac{1}{4}''$ in diameter and the tube entering the core containing trapping material would be approximately 3/16" in diameter and about 6" in length. In the tube would be a trap such as a TENAX ® trap which would be $\frac{1}{8}''$ in diameter and 4" in length, for example.

Thus, various trapping materials are useful in the practice of our invention in both the trap used in trapping the materials emitted from within the living fruit and entrapping the materials emitted from the outer surface of the living fruit. As stated, supra, TENAX ® is a preferable material. Various forms of TENAX ® are useful, for example, TENAX ® -GC. TENAX ® is a registered trademark of ENKA N.V. of The Kingdom of The Netherlands (CAS Registration No. 24938-68-9). Various forms of TENAX ® and methods of producing such forms of TENAX ® are described in the following U.S. Letters Patent, the disclosures of which are incorporated herein by reference:

U.S. Pat. No. 3,400,100 issued on Sep. 3, 1968 ("Process For The Preparation Of Polyphenylene Ethers")

U.S. Pat. No. 3,644,227 issued on Feb. 22, 1972 ("Separation Of Poly(2,6-Dimethyl-1,4-Phenyleneoxide") from its blends with other polymers))

U.S. Pat. No. 3,703,564 issued on Nov. 21, 1972 ("Bis[-Polyphenyleneoxide]-Ester Block Copolymers")

U.S. Pat. No. 4,431,779 issued on Feb. 14, 1984 ("Polyetheramide-Polyphenylene Ether Blends")

U.S. Pat. No. 4,801,645 issued on Jan. 31, 1989 ("Thermoplastic Resin Composition") TENAX ®-GC is actually a polyphenyleneoxide defined according to the structure:

wherein N is an integer of from about 100 up to about 150.

Other trapping materials are as follows: Activated Carbon marketed by Aldrich Chemical Company of 1001 West Saint Paul Avenue, Milwaukee, Wisc. 53233 (Catalog Nos. 16, 155-1; 29, 259-1; 24, 223-3; 24, 224-1 and 24, 227-6); Activated Alumina marketed by Sigma Chemical Company of St. Louis, Mo. (Catalog Nos. A8753; A8878; A9003; A1772; A1522 and A2272); Silica Gels marketed by Sigma Chemical Company, for example, Catalog Nos. S4004; S6628 and H8506; CHROMOSORB ® (registered trademark of the Johns-Manville Company of Manville, N.J.) such as CHROMOSORB ® such as LC-1; CHROMOSORB ® LC-2; CHROMOSORB ® LC-3, and CHROMOSORB ® LC-7 marketed by the Sigma Chemical Company under Catalog Nos. C 0641; C 0766, C 5517 and C 6269.

The negative pressure pump means of our invention is preferably a vacuum pump of the "Low Flow" variety, for example, "Low Flow" pumps marketed by the Ametek Company of Largo, Fla. 34643 (the Ametek Constant Flow Sampler).

DETAILED DESCRIPTION OF THE DRAWINGS

Figure 1:
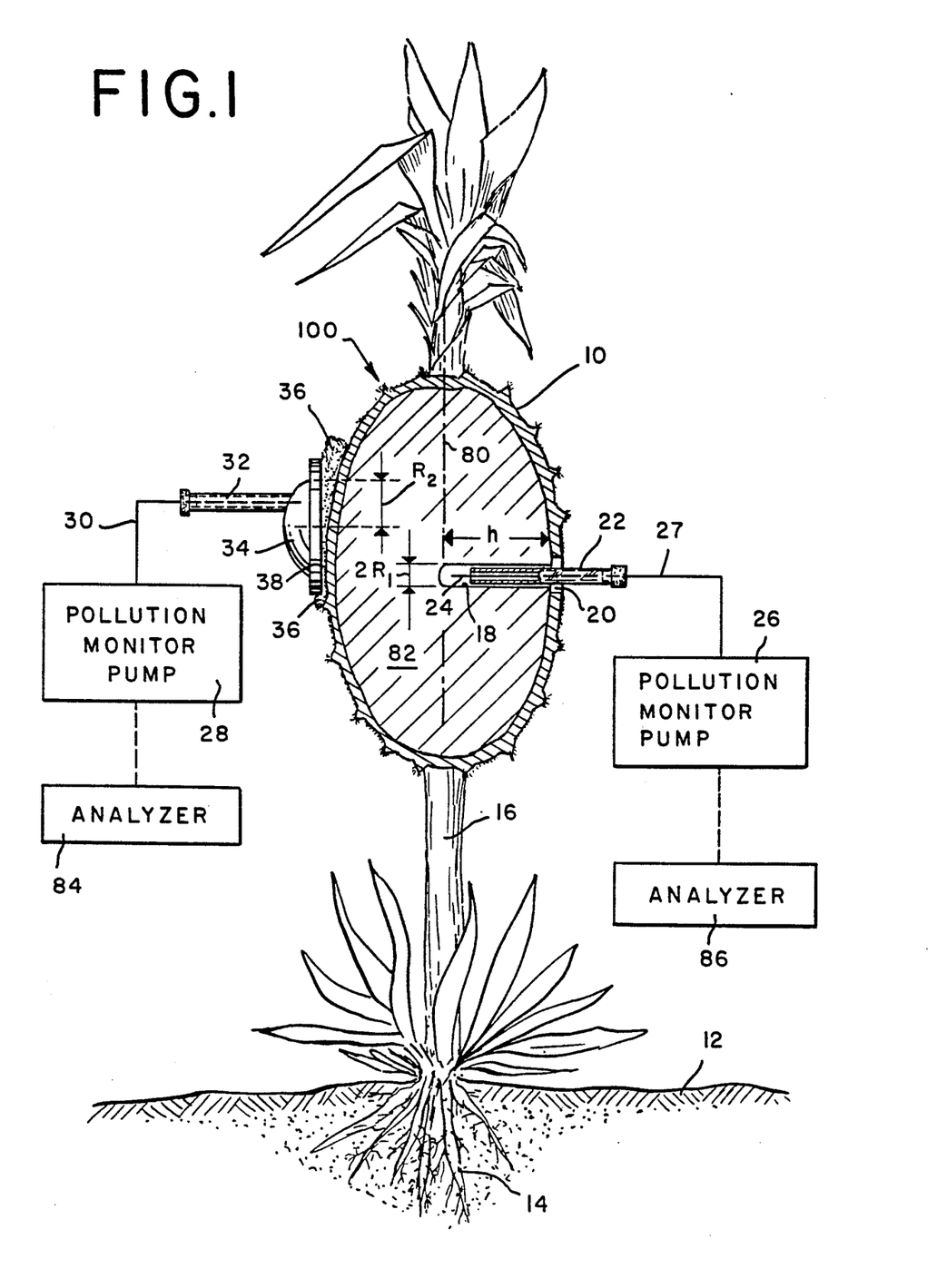
FIG. 1 is a schematic drawing showing a cut-away side elevation view of a pineapple being quantitatively and qualitatively substantially continuously analyzed for the aroma emitted and rate of emission of the components thereof:
  (i) from within; and
  (ii) from the outer surface of the pineapple simultaneously.
Figure 2:
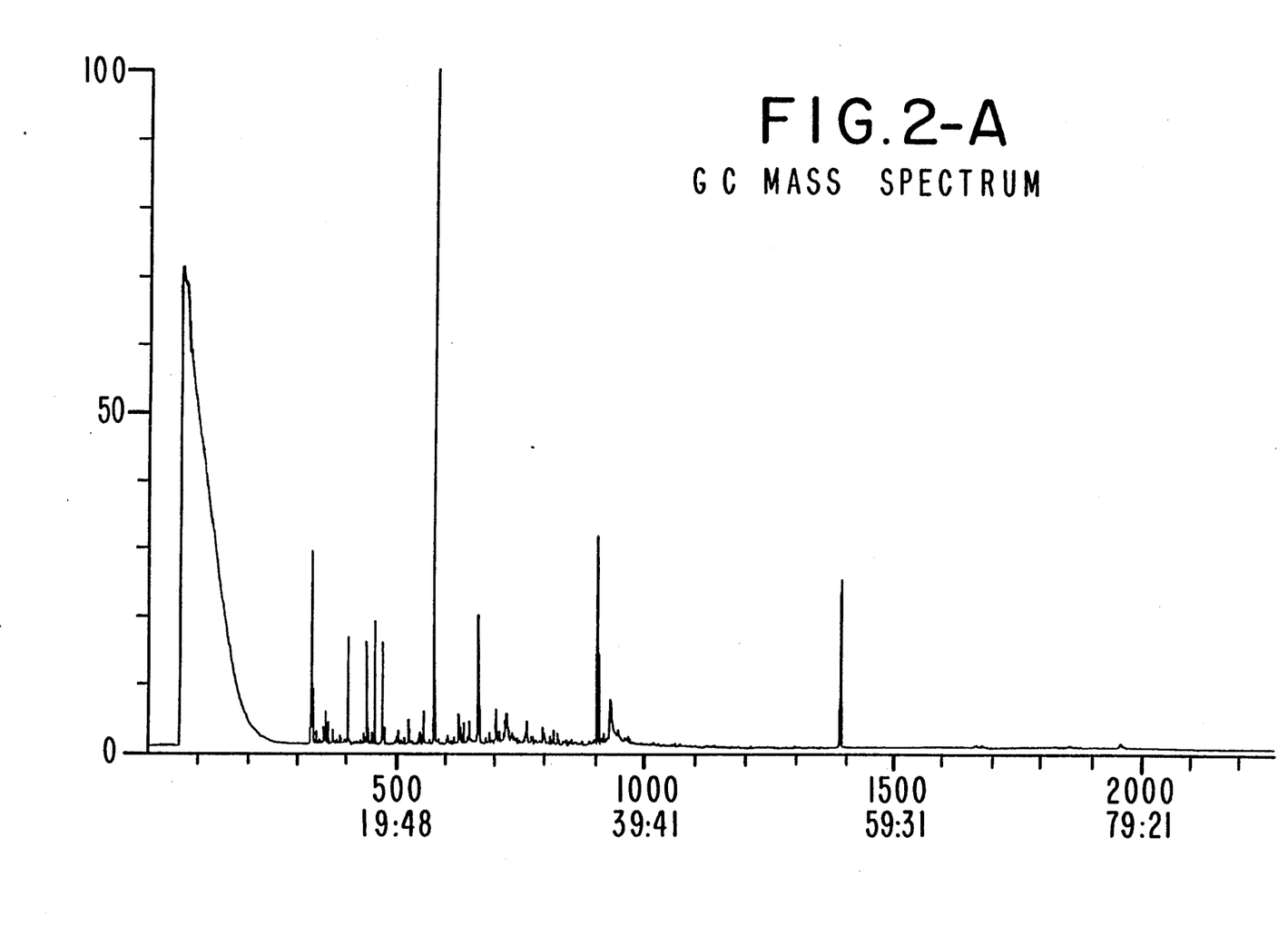
FIG. 2A is the GC mass spectrum of the composition of the aroma produced by carrying out Example I, infra, of the interior of a living pineapple.
FIG. 2B is an enlarged portion of the GC mass spectrum of FIG. 2A.
FIG. 2C is another enlarged portion of the GC mass spectrum of FIG. 2A.
Figure 3:
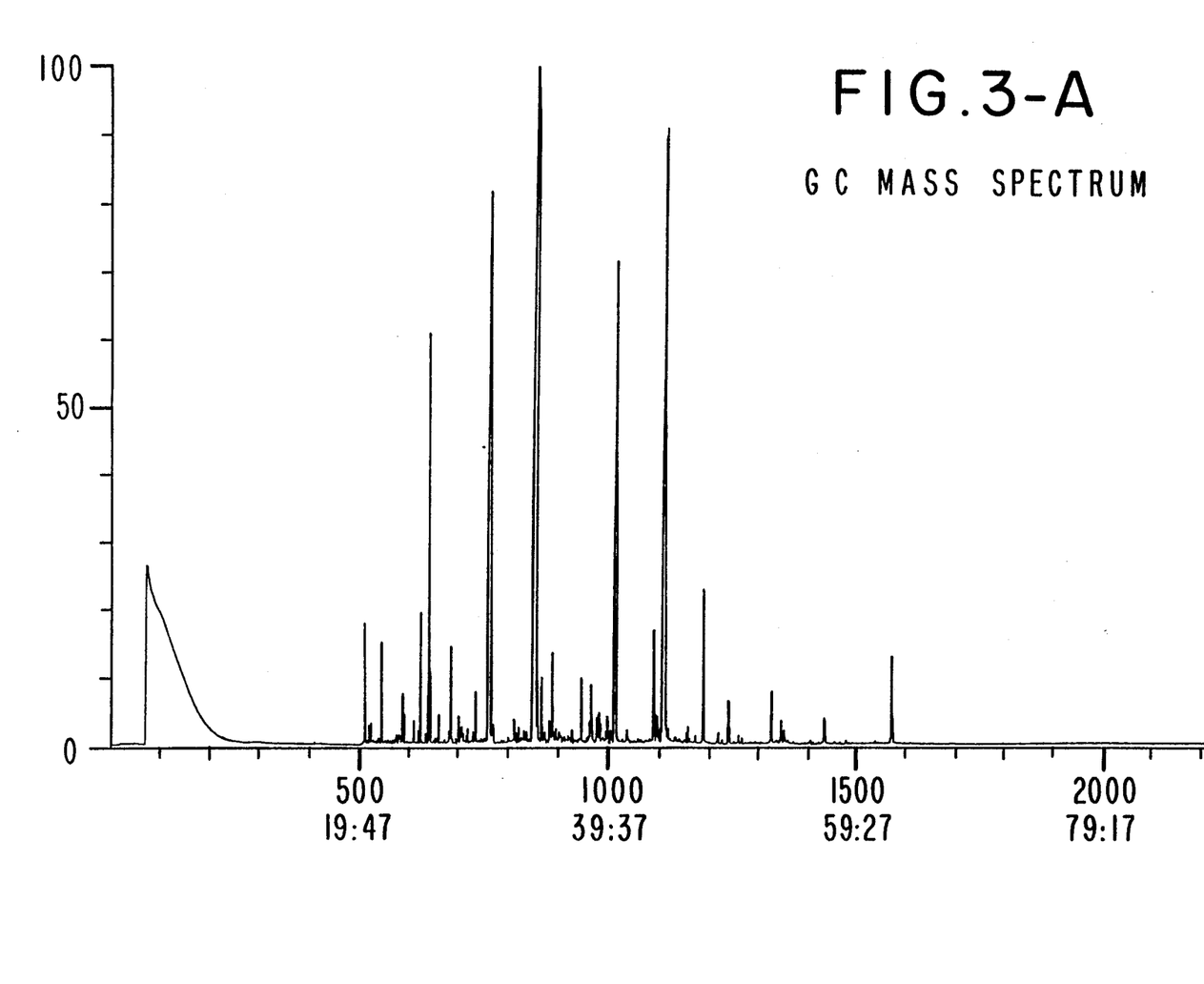
FIG. 3A is the GC mass spectrum of the aroma emitted from the external surface of a pineapple in Example 1, infra, using the apparatus shown in FIG. 1.
FIG. 3B is an enlarged portion of the GC mass spectrum of FIG. 3A.
FIG. 3C is another enlarged portion of the GC mass spectrum of FIG. 3A.

Referring to FIG. 1, a living pineapple having access 80 and roots 14 living in ground 12 having an inner volume 82 and a surface 10 is shown having the aroma and rate of emission of the components thereof:
  (i) from within the pineapple; and
  (ii) from the outer surface of the pineapple being analyzed simultaneously.

A substantial portion of the outer surface 10 is located at a given distance "h" (e.g., 6") from the central axis 80 and an inner volume 82 surrounds the central axis 80 and is encompassed by the outer surface 10; and a depth core section 18 is removed from the inner volume 82 along a directional vector "V" extending substantially radially from the central axis 80 to the outer surface 10 within the inner volume 82. The depth core section 18 has effective diameter, $D_1$ (e.g., about $\frac{1}{4}''$) equal to $2 \times$ (the effective radius, $R_1$ (about $\frac{1}{8}''$)) and a core section volume ranging from about $$[\pi R_1^2 h]$$

down to about $$\left[\frac{\pi R_1^2 h}{2}\right]$$

thereby forming a core section void within the living fruit. First analytical apparatus means in FIG. 1 comprises a first trapping tube means (22, 24) which is a glass outer tube 22 and a trapping tube 24 inserted through opening 20 into depth core 18. Attached to the trapping tube 24 (which may, for example, contain 10× ®GC) is tube 27 connected to a negative pressure pump means 26.

Reference numeral 86 represents analytical apparatus capable of providing GC-mass spectra of trapped substances which may be taken further together with spectral apparatus capable of providing infrared spectra of the trapped substances and apparatus capable of providing NMR spectra of the trapped substances.

Second analytical apparatus means (for analyzing the aroma emitted from the surface of the pineapple of FIG. 1) comprises second trapping tube means 32 inserted into enclosure 34 which is sealably affixed at 36 (a sealing material is indicated by reference numeral 36) to a portion of the surface of the pineapple 38. The trapping tube means is connected to tube 30 which is connected to negative pressure pump 28 associated with analyzer 84 (e.g., GC-mass spectral analyzer; nuclear magnetic resonance analyzer; and infrared analyzer). The apparatus is maintained in place in conjunction with the living fruit, e.g., the living pineapple of FIG. 1 which is held up by living pineapple stem 16. The trapping tube is inserted into the enclosure means (e.g., a hemispherically-shaped cup means having an inner cup means void and an outer cup means surface surrounding the void and terminating at a substantially circular rim of radius $R_2$ with the inner volume of said cup means being about:

$$\left[ \frac{2}{3} \pi R_2^3 \right].$$

Thus, when the first negative pressure pump means 26 and the second negative pressure pump means 28 are simultaneously engaged, components of the aroma evolving from the outer surface of the living fruit (e.g., the pineapple shown by reference numeral 100) are entrapped in the second trapping tube means 32 and the first trapping tube means 22 simultaneously, enabling the contents of the first trapping tube means and the second trapping tube means to be continuously analyzed substantially simultaneously using said first and second chemical analysis means 86 and 84, respectively.

The following example is illustrative of our invention but our invention is only limited by the scope of the claims following said example.

EXAMPLE I

HEAD SPACE SAMPLING AND THE ANALYSIS OF THE INTERIOR AND EXTERIOR OF A LIVING PINEAPPLE FRUIT

OBJECTIVE

To analyze the head space of the exterior and interior of a living pineapple fruit to determine, through GC/MS analysis, the difference between the interior and exterior volatile head space constituents.

PROCEDURE

A mature plant containing a ripe orange color pineapple is the subject of the investigation.

To the outside of the fruit was attached one half of a 25 ml clam shaped head space flask with inlet tube. The unevenness of the pineapple's exterior against the glass head space apparatus was filled in with kimwipe tissue to make a good seal. A TENAX ® GC head space trap was then inserted into the head space flask, and the exterior head space was sampled for approximately 6-8 hours at a flow of 30 ml/minute.

The interior of the pineapple was bored half way (3.5") with a metal ¼" diameter cork borer. A glass ¼" pyrex tube, 10" in length was inserted into the fruit in a direction towards the central axis of the fruit, halfway between the top and bottom of the fruit. The tube extends 3.5" internally in the fruit and 6.5" externally from the fruit.

A standard TENAX ® GC trap (approximately 4.5" in length) was then inserted into this ¼" diameter tube. The interior head space of the fruit was then sampled at the same time and same conditions as the exterior head space sampling.

The entrapped interior and exterior pineapple fruit head space was then analyzed by GC/MS as shown in FIGS. 2A, 2B, 2C, 3A, 3B and 3C the analysis is as follows:

| COMPOUND IDENTIFIED | EXTERIOR % | INTERIOR % |
|---|---|---|
| Acetaldehyde | .97 | 1 |
| Dichloromethane | .01 | |
| 2-Butene | .03 | |
| Ethanol | .01 | |
| Acetone | .3 | .85 |
| Furan | | .01 |
| Methyl Acetate | | .01 |
| Isoprene | .01 | |
| Acetic Acid | .1 | 1.24 |
| Ethyl Acetate | 1.17 | |
| Methyl Propionate | .02 | |
| 2-Butenal | .01 | |
| Butanol | .01 | |
| 2-Methyl Furan | .01 | .78 |
| 2-Pentanone | .01 | |
| Diacetyl (T) | | .48 |
| Methyl Isobutyrate | .01 | |
| Ethyl Acrylate | .01 | |
| 1-Hydroxy 2-Propanone (T) | | .36 |
| Ethyl Propionate | .17 | .01 |
| Methyl Butyrate | .73 | 2.77 |
| A Methyl Furan | .01 | |
| Ethyl Isobutyrate | .14 | .15 |
| Methyl Crotonate | .04 | .01 |
| Isoamyl Alcohol | .01 | |
| Isobutyl Acetate | .06 | |
| Toluene | .06 | .38 |
| Methyl 2-Methyl Butyrate | 1.79 | 2.82 |
| 2-Hexanone | .01 | |
| Hexanal | .08 | .21 |
| 2-Furan Carboxaldehyde | .01 | |
| Ethyl Butyrate | 4.8 | 3.12 |
| Methyl Valerate | .23 | .01 |
| Furfural | .01 | 3.87 |
| Methyl 3-Hydroxy Butyrate | .01 | |
| Ethyl 2-Methyl Butyrate | .44 | .87 |
| Furfuryl Alcohol | | .01 |
| Ethyl Isovalerate | .01 | |
| Hexanol | .36 | |
| Methyl Tiglate | .01 | |
| Xylene | .33 | 1.11 |
| Ethyl Valerate | | .01 |
| 3-Heptanone | .01 | |
| 2-Heptanone | .22 | |
| Isoamyl Acetate | .01 | |
| Ethyl Valerate | .69 | .01 |
| Citraconic Ahydride | | 1.22 |
| Heptanal | .01 | .71 |
| Methyl Trans-3-Hexenoate | .01 | |
| Amyl Acetate | .01 | |
| Methyl Hexanoate | 13.14 | 24.56 |
| Benzaldehyde | | .07 |
| 5-Methyl Furfural | | .3 |
| 3-Methyl 2-Butenyl Acetate | .01 | |
| Methyl Trans-3-Hexenoate | .19 | |
| Cumene | .01 | |
| Propyl Benzene | .06 | |

-continued

| COMPOUND IDENTIFIED | EXTERIOR % | INTERIOR % |
|---|---|---|
| Methyl Trans 2-Hexenoate | .07 | |
| C-3 Benzene Derivative | .64 | |
| 2-Octanone (T) | .07 | |
| Phenol | .08 | 1.25 |
| Ethyl Caproate | 25.56 | 4.74 |
| Ethyl 3-Hexenoate | .7 | |
| Cis-3-Hexenyl Acetate | | .01 |
| Myrcene | | .01 |
| Methyl Sorbate | .01 | |
| Methyl 3-Methyl Thiopropionate | .88 | .45 |
| Decane | .12 | .45 |
| Methyl Heptanoate | .16 | .01 |
| Gamma Hexalactone | .17 | |
| p-Cymene | .01 | .01 |
| 2-Ethyl Hexanol | .17 | .75 |
| Limonene | .13 | .55 |
| Ethyl 2-Hexenoate | .13 | |
| Methyl 3-Hydroxy Hexenoate (T) | .01 | |
| Decalin | .01 | |
| Octanol | .01 | |
| Ethyl Sorbate | .01 | |
| Ethyl 3-Methyl Thiopropanoate | 1.05 | |
| Alpha Para Dimethyl Styrene | .01 | |
| Ethyl Heptanoate | .7 | |
| Methyl Cis-4-Octenoate | .37 | |
| Phenyl Ethyl Alcohol | .01 | |
| Nonanal | | 1.01 |
| Linalool | | .01 |
| Ethyl 2-Ethyl Hexanoate | | .25 |
| Undecane | | .62 |
| Ethyl 3-Hydroxy Hexanoate | 1 | |
| Methyl Octanoate | 9.39 | .64 |
| Silicone | 1.83 | 8.77 |
| Ethyl Cis-4-Octenoate | .5 | |
| Ethyl Octanoate | 13.4 | .01 |
| Methyl 3,5-Acetoxy Hexanoate (T) | 5.36 | .61 |
| 5-Hydroxy Methyl Furfural | | 7.86 |
| Decanal | .07 | |
| Citronellal | | .01 |
| Ethyl HydroxyOctanoate (T) | 2.31 | |
| Ethyl Nonanoate | .01 | |
| Methyl Decanoate | .16 | |
| Ethyl Decanoate | .41 | |
| 5-Acetyloxy Methyl Octanoate (T) | .23 | |
| Alpha Muurolene | 1.34 | 1.43 |
| Alpha Copaene | | .01 |
| Alpha Caryophellene | | .01 |
| Total Percentage Identified: | 93.55 | 76.41 |

What is claimed is:

1. A process for quantitatively and qualitatively substantially continuously analyzing the aroma emitted and rate of emission of the components thereof:
   (i) from within; and
   (ii) from the outer surface of
a living fruit, simultaneously, consisting essentially of the steps of:
   (a) providing a living fruit located on a given central axis having an outer surface, a substantial portion of which is located at a given distance, "h" from said central axis and an inner volume surrounding said central axis and encompassed by said outer surface;
   (b) removing a depth core section from said inner volume running from said outer surface to a depth of from about "½h" up to "h" into said inner volume along a directional vector "v" extending substantially radially from said central axis to said outer surface within said inner volume, said depth core section having an effective diameter, $D_1$ equal to 2×(effective radius, $R_1$) and a core section volume ranging from about $$[\pi R_1^2 h]$$

down to about $$\left[\frac{\pi R_1^2 h}{2}\right]$$

thereby forming a core section void within said living fruit; then
   (c)-1: providing first analytical apparatus means comprising first trapping tube means attached to first negative pressure pump means associated with first chemical analysis means;
   (c)-2: providing second analytical apparatus means comprising a second trapping tube means attached to second negative pressure pump means associated with second chemical analysis means:
   (d) providing a hollow flexible enclosure means having an inner enclosure means void and an outer enclosure means surface encompassing said void and terminating at an enclosure rim means, said void being defined by said outer enclosure means surface and said enclosure rim means, an insertion orifice extending from said outer enclosure means surface to said inner enclosure means void, said enclosure means being capable of sealably gripping an unbroken portion of said outer surface of said living fruit at said enclosure rim means;
   (e) causing said enclosure means to sealably grip said portion of said outer surface of said living fruit at said enclosure rim means;
   (f) inserting said first trapping tube means into said core section void along said directional vector "v";
   (g) inserting said second trapping tube means through said insertion orifice, causing it to be extended into said enclosure means void;
   (h) simultaneously engaging said first negative pressure pump means and said second negative pressure pump means whereby components of the aroma evolving from said outer surface of said living fruit are entrapped in said second trapping tube means and components of the aroma evolving from within said living fruit are entrapped in said first trapping tube means, simultaneously; and
   (j) analyzing the contents of said first trapping tube means using said first chemical analysis means and said second trapping tube means using said second chemical analysis means substantially continuously and substantially simultaneously.

2. Apparatus for quantitatively and qualitatively substantially continuously analyzing the aroma evolved:
   (i) from within; and
   (ii) from the outer surface of
a living fruit, simultaneously, consisting essentially of:
   (a) a living fruit located on a given central axis having an outer surface, a substantial portion of which is located at a given distance, "h" from said central axis; an inner volume surrounding said central axis and encompassed by said outer surface; a depth core section removed from said inner volume running from said outer surface to a depth of from about "½h" up to "h" into said inner volume along a directional vector "v" extending substantially radially from said central axis to said outer surface within said inner volume, said depth core section having an effective diameter $D_1$ equal to $2\times$(effective radius, $R_1$) and a core section volume ranging from about $$[\pi R_1^2 h]$$

down to about $$\left[\frac{\pi R_1^2 h}{2}\right]$$

thereby forming a core section void within said living fruit;

(b)-1: first analytical apparatus means comprising first trapping tube means attached to first negative pressure pump means associated with first chemical analysis means;

(b)-2: second apparatus means comprising second trapping tube means attached to second negative pressure pump means associated with second chemical analysis means;

(c) hollow flexible enclosure means having an inner enclosure means void and an outer enclosure means surface encompassing said void and terminating at an enclosure rim means, said void being defined by said outer enclosure means surface and said enclosure rim means, an insertion orifice extending from said outer enclosure means surface to said inner enclosure means void, said enclosure means sealably gripping an unbroken portion of said outer surface of said living fruit at said enclosure rim means;

(d) said first trapping tube means being inserted into said core section void along said directional vector "v";

(e) said second trapping tube means being inserted through said insertion orifice, causing it to be extended into said enclosure means void;

whereby when said first negative pressure pump means and said second negative pressure pump means are simultaneously engaged, components of the aroma evolving from said outer surface of said living fruit are entrapped in said second trapping tube means and components of the aroma evolving from within said living fruit are entrapped in said first trapping tube means, simultaneously, enabling the contents of said first trapping tube means and said second trapping tube means to be continuously analyzed substantially simultaneously using said first and second chemical analysis means.

3. The apparatus of claim 2 wherein the hollow flexible enclosure means is a hemispherically-shaped cup means having an inner cup means void and an outer cup means surface surrounding said void and terminating at a substantially circular rim of radius $R_2$, with the inner volume of said cup means being about $$\left[\frac{2}{3}\pi R_2^3\right].$$

4. The process of claim 1 wherein the living fruit is a living pineapple.

5. The process of claim 1 wherein the living fruit is a living nectarine.

6. The apparatus of claim 2 wherein the living fruit is a living pineapple.

7. The apparatus of claim 2 wherein the living fruit is a living nectarine.

* * * * *